(12) United States Patent
Flick

(10) Patent No.: US 10,130,551 B2
(45) Date of Patent: Nov. 20, 2018

(54) CONDOM AND CLITORIS STIMULATION APPARATUS

(71) Applicant: Conrad Flick, Bettendorf, IA (US)

(72) Inventor: Conrad Flick, Bettendorf, IA (US)

( * ) Notice: Subject to any disclaimer, the term of this patent is extended or adjusted under 35 U.S.C. 154(b) by 167 days.

(21) Appl. No.: 14/243,978

(22) Filed: Apr. 3, 2014

(65) Prior Publication Data

US 2014/0303433 A1    Oct. 9, 2014

Related U.S. Application Data

(60) Provisional application No. 61/808,207, filed on Apr. 3, 2013.

(51) Int. Cl.
*A61H 19/00* (2006.01)
*A61F 6/04* (2006.01)

(52) U.S. Cl.
CPC .............. *A61H 19/50* (2013.01); *A61F 6/04* (2013.01); *A61H 19/40* (2013.01); *A61F 2006/047* (2013.01); *A61F 2006/048* (2013.01); *A61H 2201/165* (2013.01); *A61H 2201/1688* (2013.01)

(58) Field of Classification Search
CPC ...... A61H 19/34; A61H 19/50; A61B 17/326; A61F 6/04; A61F 2005/411; A61F 2005/412; A61F 2/105; A61F 2/26; A61F 5/41
See application file for complete search history.

(56) References Cited

U.S. PATENT DOCUMENTS

| 2006/0041310 A1* | 2/2006 | Williams | A61F 2/26 623/15.12 |
| 2010/0016656 A1* | 1/2010 | Rudi | A61F 5/41 600/39 |

* cited by examiner

*Primary Examiner* — Christine H Matthews
(74) *Attorney, Agent, or Firm* — Bradford E. Kile; Scott Houtteman; Kile Park Reed & Houtteman PLLC

(57) ABSTRACT

A condom features a generally cylindrical sheath with an open proximal end and a distal end that fits onto a male penis. The condom also features a tether which is connected at the distal end of the sheath. The tether has an axial length greater than the axial length of the sheath and is designed to be grasped by a female partner during intercourse and placed into a rubbing contact with the clitoris.

11 Claims, 4 Drawing Sheets

CONDOM AND CLITORIS STIMULATION APPARATUS

This application claims the benefit of U.S. Provisional Application No. 61/808,207, filed Apr. 3, 2013.

BACKGROUND OF THE INVENTION

Field of the Invention

The present invention relates to a condom for contraceptive and prophylactic use, and ultimately, enhanced pleasure. In particular, this invention relates to an improved condom for vaginal intercourse which encourages its use beyond merely for prevention and protection.

The use of conventional condoms for contraceptive and prophylactic use has been known for years. The present invention is directed to overcoming the negative stigma of traditional condom use by providing an alternative use technique which heightens pleasure beyond natural intercourse. Sexually transmitted diseases are a public health concern that affects all people, regardless of nationality and age group. The medical profession, along with governmental and health organizations, strongly advocate the use of condoms to prevent unplanned pregnancies and the spread of sexually transmitted diseases, including the human immunodeficiency virus (HIV) that can result in acquired immune deficiency syndrome (AIDS).

The male condom is donned on the penis of the male partner during sexual intercourse. The typical male condom is a snug fitting, elongated tubular sheath emulating the natural contours of the penis. It has an open, proximal end for the insertion of the penis, and a closed, distal end to receive the ejaculate of seminal fluids. Typically, conventional condoms are produced using a dip molding process with glass formers to achieve a wall thinness to maximize tactile sensations through the material. The open, proximal end has a peripheral bead for rigidity to assist donning and doffing, and ultimately, constrictively securing the condom on the penis. The condom material barrier and the agents within the lubricant provide a very substantial shield. These agents include spermicides and microbicides which inactivate or block infection by sexually transmitted pathogens.

Several condoms have been developed with various irregularities on an otherwise smooth, exterior surface to stimulate the female anatomy for heightened pleasure. They include ridges, blisters, bunched-up excess material, and protrusions. However, the thin flaccid membrane lacks sufficient structural rigidity to retain any effective shape minimizing their effectiveness.

During intercourse, the female participant only receives tactile stimulation of the vulva and perineum regions at the moment of full penetration by the male. Thus, most of the various textures and projections about the proximal condom opening are relatively non-effective for sustained, female stimulation.

The difficulties and limitations suggested in the preceding and desired features are not intended to be exhaustive but rather are among many which may tend to reduce the effectiveness and user satisfaction with condoms. Other noteworthy problems and limitations may also exist; however, those presented above should be sufficient to demonstrate that condoms appearing in the past will admit to worthwhile improvement.

BRIEF SUMMARY

One preferred embodiment of the invention which is intended to address concerns and accomplish at least some of the foregoing objectives comprises a condom capable of being dip molded using glass formers to achieve wall thinness and its unique characteristics. This embodiment possesses a tether extending from the distal region of the condom body of sufficient length to allow a participant to grasp during sexual intercourse. Preferably, the tether is simply an axial or angular extension of the condom body with a diminished diameter, or may be a separate piece attached at or near the distal region of the body. This allows the tether attachment point to stay within the vagina or near the vaginal opening during the male's partial withdrawal to ensure vulva region contact and sustained stimulation, and the positioning of the condom on the penis. The tether can have several different surface configurations, from very aggressive to extremely subtle, for varied levels of stimulation.

DRAWINGS

Other objects and advantages of the present invention will become apparent from the following detailed description of preferred embodiments thereof taken in conjunction with the accompanying drawings wherein.

DETAILED DESCRIPTION

Figure 1:
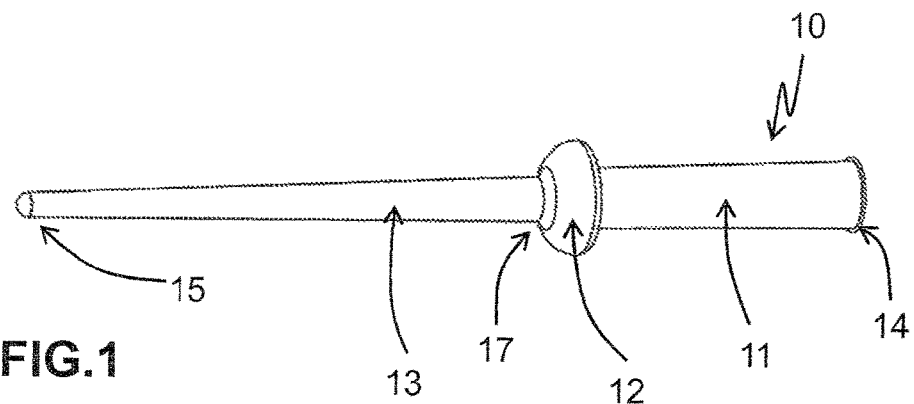
FIG. 1 is an axonometric view of a condom in accordance with one embodiment of the subject invention.

Referring now particularly to the drawings, wherein like reference characters refer to like parts, and initially to FIG. 1, there will be seen an axonometric view of the condom 10 in accordance with a preferred embodiment of the invention. The condom 10 in FIG. 1 is to be donned by the male participant about his penis. This condom 10 has a sheath body 11 with a distal end 12 and an open, proximal end 14. At the distal end 12, a tether 13 extends axially from the body sheath 11. The distal end 15 of tether 14 is preferably closed. At the open proximal end 14, the condom 10 has a beaded cuff 16 formed by back-rolling cuff material. This cuff 16 provides rigidity to assist in donning and doffing the condom 10, and constrictively securing the condom 10 about the penis. In the distal region 12 of condom 10, there is an enlarged section 17 designed to entrap the head of the penis when the tether 14 is pulled in an opposing direction to the penis caused by being within the vagina. This region is also for the containment of ejaculated seminal fluids. The juncture 18 of the condom body 11 and tether 14 is a seamless continuation of the wall material. Both the tether 13 and the condom body 11 taper towards their distal ends, 15 and 12. The axial alignment with draft greatly facilitates stripping the finished condom 11 from the dipping former.

Figure 2:
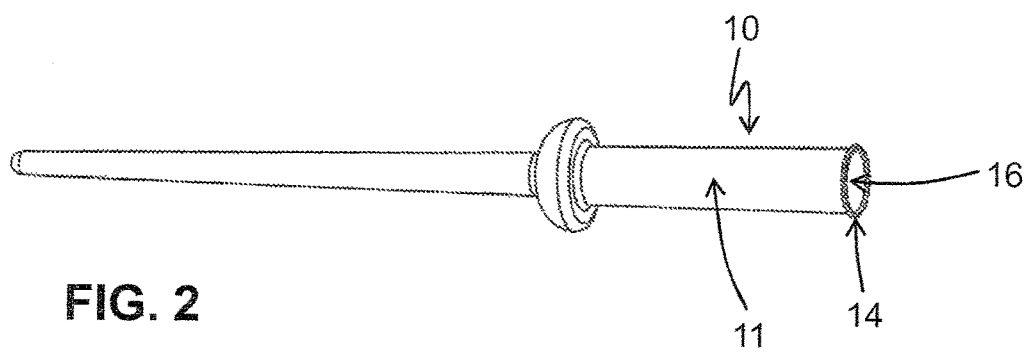
FIG. 2 is another axonometric view of the same condom

The axonometric view of condom 10 in FIG. 2 reveals the proximal open end of the sheath 11 banded by the beaded cuff 16.

Figure 3:
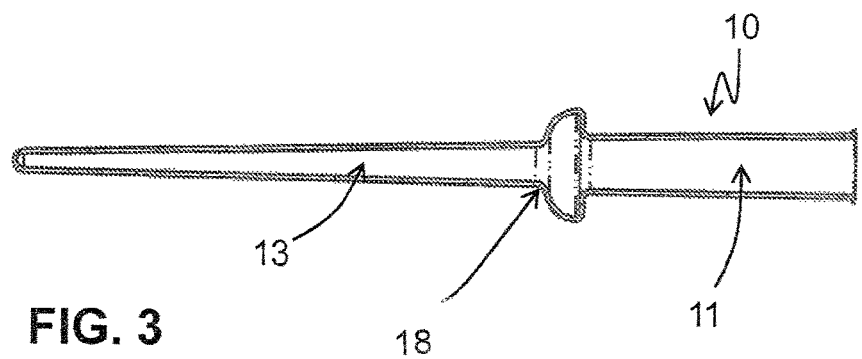
FIG. 3 is a cross sectional view of FIG. 1.

The cross-sectional view of condom 10 in FIG. 3 displays the seamless juncture 18 in the wall structures of the sheath body 11 and tether 13.

Figure 4:
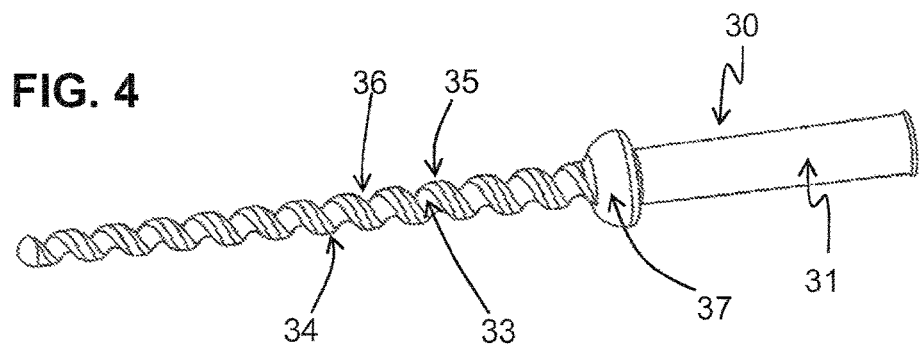
FIG. 4 is an axonometric view of a condom in accordance with the preferred embodiment of the subject invention; the main variation is the tether geometry.

FIG. 4 shows a condom 30 with a similar sheath structure 31 and a varied textured tether 33. In this tether 33 has a helical "drill bit" geometry 34 to create sustained, random surfaces from ridges 35 and valleys 36 for stimulation of the vulva region and clitoris of a female partner during thrusting intercourse.

Figure 5:
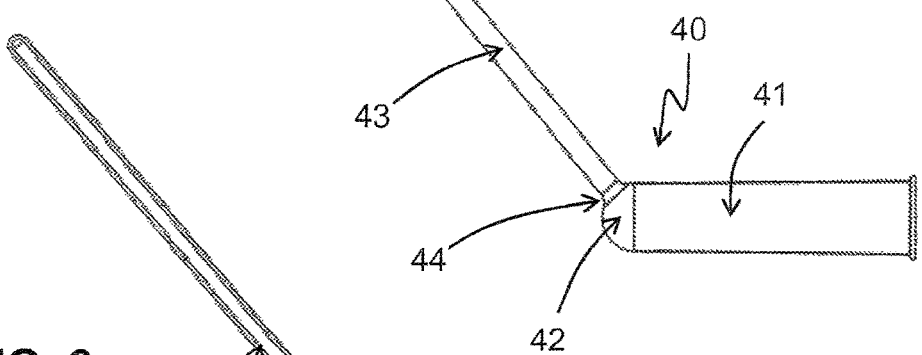
FIG. 5 is a side view of an alternative with an angled tether.
Figure 6:
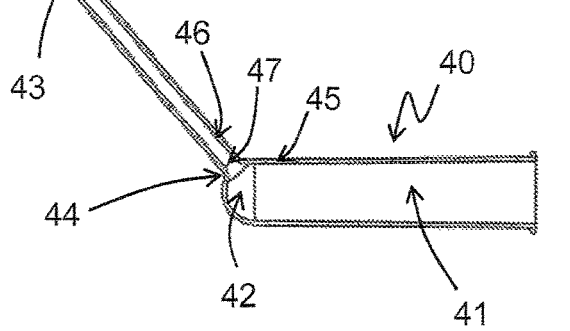
FIG. 6 is a cross sectional view of FIG. 5.

A side view of condom 40 in FIG. 5 illustrates an angular tether 43 extending at approximately a 45 degree angle with respect to an imaginary central longitudinal axis of the sheath body 41 which is integrally molded onto a distal region 42 of sheath body 41. Juncture 44 of the tether 43 is a seamless continuation in the wall structure of the sheath 41 and the tether 43, as revealed in cross-sectional view FIG. 6. In this embodiment of the subject condom the sheath does not have an enlarged area at the distal region 42 and instead relies on the pliable nature of the thin material 45 for entrapment of the head of the penis when the tether 43 is pulled in an opposing direction to the penis caused by being within the vagina. Seminal fluid is contained within a base region 47 of the integral tether 43.

Figure 7:
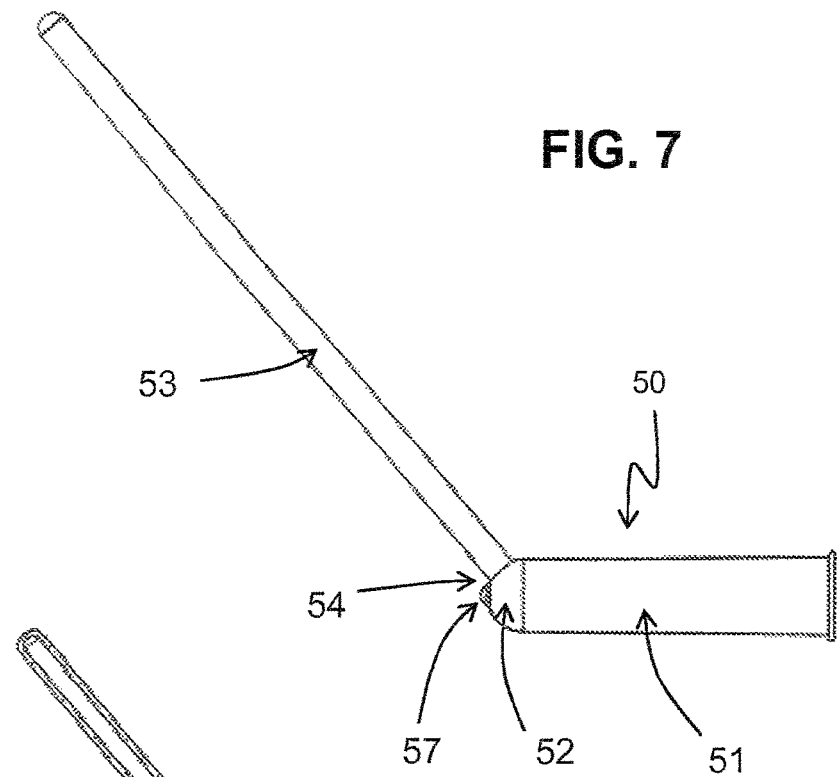
FIG. 7 is a side view of an alternative embodiment; the main variation is the tether mechanical attachment to the body.
Figure 8:
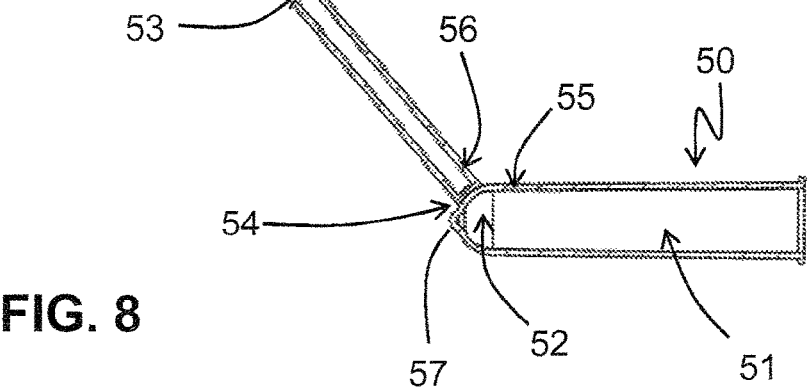
FIG. 8 is a cross section view of FIG. 7.

FIG. 7 depicts a condom 50 with a body sheath 51 and a separate tether 53 that is attached, as opposed to being integral, with the body sheath 51. The condom body sheath 51 and a separate tether 53 with a domed distal end 37 are separately dip molded and then physically attached at juncture 54. The distinct, separate walls of the body sheath 55 and the tether 53 are shown in the cross-sectional view in FIG. 8. The secure juncture 54 may be constructed thermally or with an adhesive. There is a provisional blister 57 in the distal region 52 of the sheath 51 for containment of seminal fluid.

Figure 9:
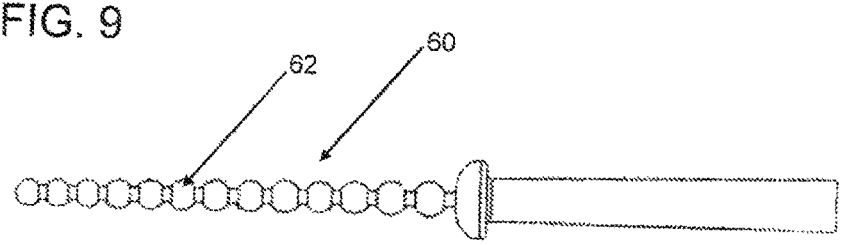
FIGS. 9 and 10 are alternative embodiments of the invention where the tether extension is provided with transverse balls or ribs for enhanced clitoris stimulation during intercourse.
Figure 10:
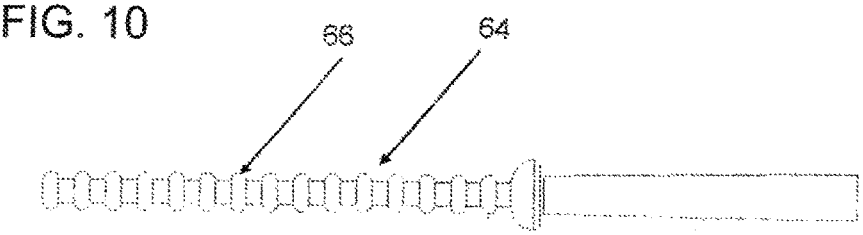

FIGS. 9 and 10 disclose yet other embodiments of the invention where a tether extension 60 or 64 may be a flat strip with a series of transversely extending serially spaced balls 62 in FIG. 9 and transverse ribs 66 in FIG. 10.

In use the subject condom is designed to be worn by a male partner with the tether extending in a reverse fold posture along the top of the condom upon insertion during intercourse. A female partner grasps the distal end of the tether and by gentle pulling on the end of the tether is able to control the pressure of the tether structure gliding across the female clitoris as the male partner thrusts in a conventional missionary intercourse position. The condom is composed of any conventional condom composition and the tether is fabricated with the same material as the condom such as for example a latex rubber composition or other materials having elastic characteristics.

In describing the invention, reference has been made to preferred embodiments and illustrative advantages of the invention. Those skilled in the art, however, and familiar with the instant disclosure of the subject invention may recognize additions, deletions, modifications, substitutions and other changes that will fall within the purview of the subject claims.

What is claimed is:

1. A condom and vulva region stimulation apparatus comprising:
    a generally cylindrical, tubular, condom sheath operable for use as a condom during vaginal intercourse having an open proximal end and an open distal end and being operable to be fitted onto and generally over a male penis; and
    a generally tubular, tether means having a closed first end and a second end and said second end connected to, and forming a monolithic apparatus with, the distal end of said condom sheath, said tether means extending away from said generally cylindrical, tubular, condom sheath, said tether means having a textured outer surface and an axial length generally greater than an axial length of said generally cylindrical condom sheath and said first end of said tether means being operable to be grasped by a female partner during intercourse and tensioned by the female partner to apply rubbing contact by said textured outer surface of said tether means with the female partner vulva region during intercourse.

2. The condom and vulva region stimulation apparatus as defined in claim 1 wherein:
    said tether means comprises a monolithic longitudinal tubular extension of said condom sheath and extending from said condom sheath a distance from said condom sheath at least twice as long as said condom sheath and said tether means having an exterior surface means operable for translation over and stimulation of the female vulva region during intercourse.

3. The condom and vulva region stimulation apparatus as defined in claim 1 wherein:
    said tether means axial length is twice as long as the axial length of said condom sheath.

4. The condom and vulva region stimulation apparatus as defined in claim 1 wherein:
    said tether means comprises an integral tubular extension of said condom sheath and extending from said condom sheath a distance from said condom sheath at least twice as long as said condom sheath.

5. The condom and vulva region stimulation apparatus as defined in claim 1 wherein:
    said tether means is generally circular in cross-section and decreases in diameter from a proximal end to a distal end of said tether means.

6. The condom and vulva region stimulation apparatus as defined in claim 1 wherein:
    said tether means has a generally helical longitudinal geometry operable to create a series of surfaces of ridges and valleys for stimulation of a vulva region of the female partner during thrusting intercourse.

7. The condom and vulva region stimulation apparatus as defined in claim 1 wherein:
    said tether means comprises a flexible strip connecting a series of axially aligned ball structures.

8. The condom and vulva region stimulation apparatus as defined in claim 1, wherein:
    said tether means is longitudinally elastic and is operable to be elastically stretched and released for retraction by the female partner for stimulation of the female partner's vulva region during intercourse.

9. The condom and vulva region stimulation apparatus as defined in claim 1, wherein:
    said tether means includes a plurality of transverse ridges extending in spaced intervals transversely generally along the length of said tether means to provide enhanced rubbing contact by the transverse ridges of said tether means with the female partner's vulva region during intercourse.

10. A condom and vulva region stimulation apparatus comprising:

a generally cylindrical sheath having an open proximal end and a closed distal end and being operable to be fitted onto a male penis; and a tether connected generally at said closed distal end of said generally cylindrical sheath, said tether having a textured exterior surface and an axial length greater than an axial length of said sheath and extending at approximately a forty five degree angle with respect to said sheath and being operable to be grasped by a female partner during intercourse and tensioned by the female partner to operably apply rubbing contact by said tether exterior surface with the vulva region of the female partner during intercourse, wherein:

said tether has a helical longitudinal geometry operable to create a series of surfaces of ridges and valleys for stimulation of the vulva region of the female partner during thrusting intercourse.

11. A condom and vulva region stimulation apparatus comprising:

a generally cylindrical sheath having an open proximal end and a closed distal end and being operable to be fitted onto a male penis; and a tether connected generally at said closed distal end of said generally cylindrical sheath, said tether having a textured exterior surface and an axial length greater than an axial length of said sheath and extending at approximately a forty five degree angle with respect to said sheath and being operable to be grasped by a female partner during intercourse and tensioned by the female partner to operably apply rubbing contact by said tether exterior surface with the vulva region of the female partner during intercourse, wherein:

said tether comprises a flexible strip connecting a series of axially aligned ball structures.

\* \* \* \* \*